United States Patent
Park et al.

(10) Patent No.: US 10,532,546 B2
(45) Date of Patent: Jan. 14, 2020

(54) COMPOSITE FOR NEUTRAL LAYER

(71) Applicant: LG Chem, Ltd., Seoul (KR)

(72) Inventors: No Jin Park, Daejeon (KR); Sung Soo Yoon, Daejeon (KR); Jung Keun Kim, Daejeon (KR); Je Gwon Lee, Daejeon (KR); Mi Sook Lee, Daejeon (KR)

(73) Assignee: LG Chem, Ltd. (KR)

( * ) Notice: Subject to any disclaimer, the term of this patent is extended or adjusted under 35 U.S.C. 154(b) by 83 days.

(21) Appl. No.: 15/578,951

(22) PCT Filed: Jun. 7, 2016

(86) PCT No.: PCT/KR2016/005978
§ 371 (c)(1),
(2) Date: Dec. 1, 2017

(87) PCT Pub. No.: WO2016/195449
PCT Pub. Date: Dec. 8, 2016

(65) Prior Publication Data
US 2018/0170023 A1    Jun. 21, 2018

(30) Foreign Application Priority Data

Jun. 4, 2015   (KR) .......................... 10-2015-0079454

(51) Int. Cl.
*B32B 27/08*    (2006.01)
*B32B 27/06*    (2006.01)
(Continued)

(52) U.S. Cl.
CPC ............ *B32B 27/302* (2013.01); *A61P 35/00* (2018.01); *B32B 3/26* (2013.01); *B32B 27/30* (2013.01); *B32B 27/308* (2013.01); *B82Y 30/00* (2013.01); *C07D 209/48* (2013.01); *C07D 215/48* (2013.01); *C07D 303/02* (2013.01);
(Continued)

(58) Field of Classification Search
None
See application file for complete search history.

(56) References Cited

U.S. PATENT DOCUMENTS 8,691,925 B2 *  4/2014  Wu .................... C08F 293/00
                                                526/319
2012/0273460 A1  11/2012  Kang et al.
(Continued)

FOREIGN PATENT DOCUMENTS

CN    102757520 A    10/2012
CN    103797066 A     5/2014
(Continued)

OTHER PUBLICATIONS

Search report from International Application No. PCT/KR2016/005978, dated Aug. 24, 2016.
(Continued)

*Primary Examiner* — Tae H Yoon
(74) *Attorney, Agent, or Firm* — Lerner, David, Littenberg, Krumholz & Mentlik, LLP

(57) ABSTRACT

The present application relates to a neutral layer composition. The present application can provide a neutral layer composition capable of forming a neutral layer, which can be effectively applied in the formation of a polymeric film comprising a vertically aligned self-assembled block copolymer.

10 Claims, 1 Drawing Sheet

(51) Int. Cl.

| | | |
|---|---|---|
| *B32B 27/30* | (2006.01) | |
| *C08L 53/00* | (2006.01) | |
| *C08F 212/08* | (2006.01) | |
| *C08F 220/10* | (2006.01) | |
| *A61P 35/00* | (2006.01) | |
| *C07D 215/48* | (2006.01) | |
| *B32B 3/26* | (2006.01) | |
| *C08F 8/50* | (2006.01) | |
| *C08F 226/06* | (2006.01) | |
| *C08F 299/04* | (2006.01) | |
| *C08L 53/02* | (2006.01) | |
| *B82Y 30/00* | (2011.01) | |
| *C08F 12/22* | (2006.01) | |
| *C08F 220/14* | (2006.01) | |
| *C08F 293/00* | (2006.01) | |
| *C09D 153/00* | (2006.01) | |
| *C07D 209/48* | (2006.01) | |
| *C07D 303/02* | (2006.01) | |
| *G03F 7/00* | (2006.01) | |
| *C07C 255/03* | (2006.01) | |
| *B82Y 40/00* | (2011.01) | |

(52) U.S. Cl.
CPC ............... *C08F 8/50* (2013.01); *C08F 12/22* (2013.01); *C08F 212/08* (2013.01); *C08F 220/10* (2013.01); *C08F 220/14* (2013.01); *C08F 226/06* (2013.01); *C08F 293/005* (2013.01); *C08F 299/0492* (2013.01); *C08L 53/00* (2013.01); *C08L 53/025* (2013.01); *C09D 153/00* (2013.01); *G03F 7/0002* (2013.01); *B32B 2255/26* (2013.01); *B32B 2270/00* (2013.01); *B82Y 40/00* (2013.01); *C07B 2200/13* (2013.01); *C07C 255/03* (2013.01); *C08F 2438/03* (2013.01); *C08F 2810/50* (2013.01); *C08L 2203/16* (2013.01)

(56) References Cited

U.S. PATENT DOCUMENTS

| | | |
|---|---|---|
| 2013/0078576 A1 | 3/2013 | Wu et al. |
| 2013/0330668 A1 | 12/2013 | Wu et al. |
| 2014/0030652 A1 | 1/2014 | Senzaki et al. |
| 2014/0263175 A1* | 9/2014 | Gopalan .................... C08J 7/04 216/49 |
| 2014/0378592 A1 | 12/2014 | Trefonas, III et al. |
| 2015/0225850 A1* | 8/2015 | Arora ................. C23C 16/45525 216/51 |
| 2016/0186001 A1* | 6/2016 | Hustad ................. C09D 153/00 427/379 |

FOREIGN PATENT DOCUMENTS

| | | |
|---|---|---|
| CN | 104231514 A | 12/2014 |
| JP | H083270 A | 1/1996 |
| JP | 2014528015 A | 10/2014 |
| KR | 20110018678 A | 2/2011 |
| KR | 20120122655 A | 11/2012 |
| KR | 20140063790 A | 5/2014 |
| KR | 20140146881 A | 12/2014 |
| WO | 2012036121 A1 | 3/2012 |
| WO | 2015091047 A1 | 6/2015 |

OTHER PUBLICATIONS

Extended European Search Report including Written Opinion for Application No. EP16803802.4 dated Dec. 12, 2018.
Chinese Search Report for Application No. CN 201680039982.2 dated Jun. 28, 2019.

\* cited by examiner

[Figure 1]
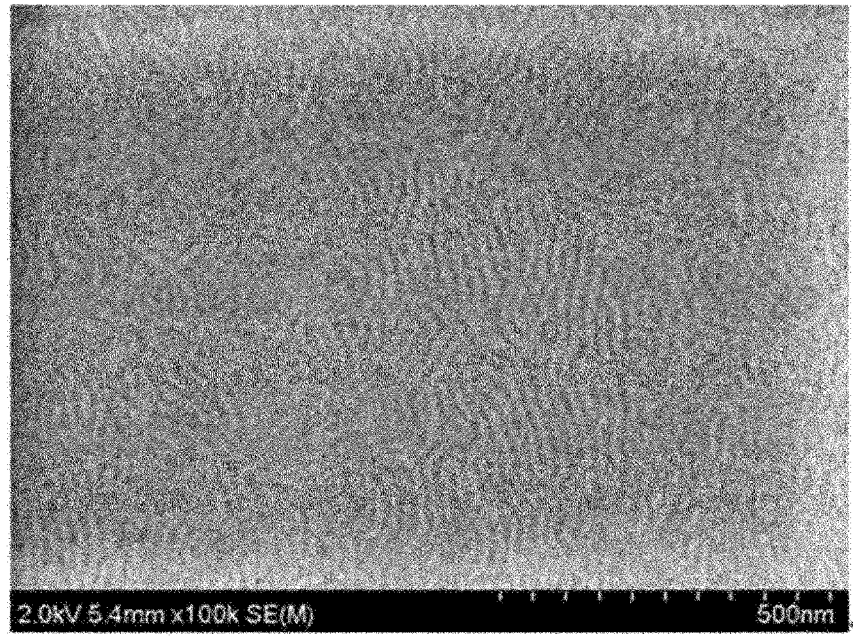
[Figure 2]
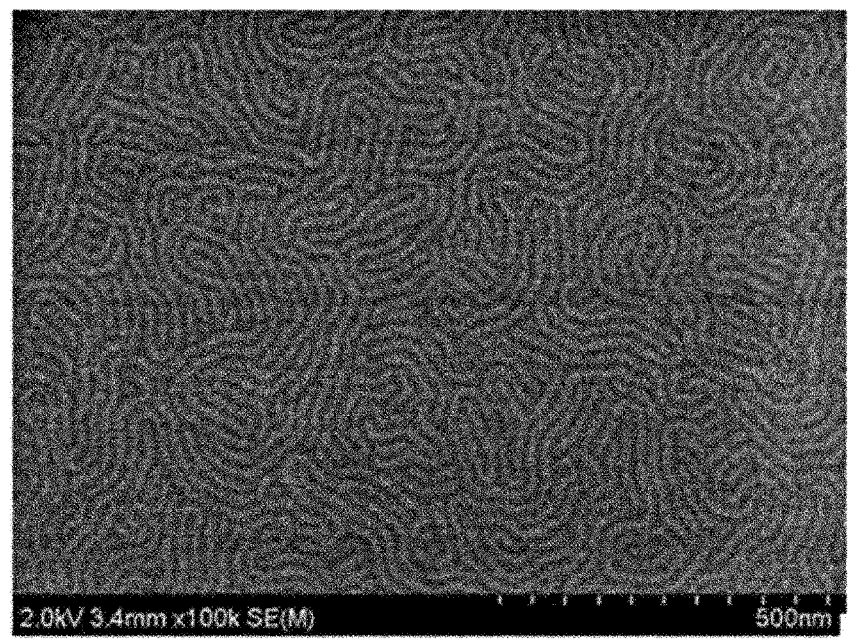

COMPOSITE FOR NEUTRAL LAYER

CROSS-REFERENCE TO RELATED APPLICATIONS

The present application is a national phase entry under 35 U.S.C. § 371 of International Application No. PCT/KR2016/005978 filed on Jun. 7, 2016, which claims priority from Korean Patent Application No. 10-2015-0079454 filed on Jun. 4, 2015, the disclosures of which are incorporated herein by reference.

TECHNICAL FIELD

The present application relates to a composition for a neutral layer.

BACKGROUND ART

Block copolymers in which two or more chemically distinct polymer chains are linked by covalent bonds can be separated into regular microphases due to their self assembly characteristics. The microphase separation phenomenon of such a block copolymer is generally explained by volume fractions, molecular weights and mutual attraction coefficients (Flory-Huggins interaction parameter) between constituents, and it may form various structures with nano-scale spheres, cylinders, gyroids or lamellae, and the like.

An important issue in practical applications of various nanostructures formed by the block copolymers is to control orientation of microphases of the block copolymer. If the spherical block copolymer nanostructure is a zero-dimensional structure having no direction of special orientation, the cylindrical or lamellar nanostructure has orientation as one-dimensional and two-dimensional structures, respectively. Typical orientation properties of the block copolymer may include a parallel orientation in which the orientation of the nanostructure is parallel to the substrate direction and a vertical orientation in which the orientation of the nanostructure is vertical to the substrate direction, where the vertical orientation often has greater importance than the parallel orientation.

Typically, the orientation of the nanostructure in the film of the block copolymer can be determined by whether any one of the blocks of the block copolymer is exposed to the surface or air. That is, the orientation of the nanostructure can be determined by selective wetting of the relevant block, where since a plurality of substrates is generally polar and air is non-polar, a block having a larger polarity in a block copolymer is wetted on a substrate and a block with a smaller polarity is wetted at the interface with air, whereby the parallel orientation is induced.

DISCLOSURE

Technical Problem

The present application provides a neutral layer composition.

Technical Solution

The present application relates to a neutral layer composition. In the present application, the term neutral layer composition may mean a composition used in forming a neutral layer. Also, in the present application, the term neutral layer may mean any kind of layer capable of inducing the vertical orientation of a block copolymer.

The neutral layer composition may comprise a certain random copolymer. The random copolymer may comprise a unit represented by Formula 1 below.

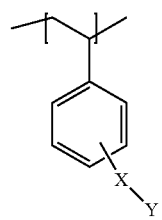

[Formula 1]

In Formula 1, X is a single bond, an alkylene group, an oxygen atom, —C(=O)—, —OC(=O)—, —C(=O)—O— or a divalent linker represented by Formula 2 below, and Y is a monovalent hydrocarbon group having 3 to 30 carbon atoms.

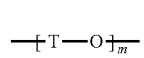

[Formula 2]

In Formula 2, T is a divalent hydrocarbon group, and m is a number within a range of 1 to 5.

The term single bond herein may mean that there is no separate atom in the relevant part. Therefore, if X is a single bond in Formula 1 above, X is absent and Y is directly linked to a benzene ring.

The term alkylene group herein may mean an alkylene group having 1 to 20 carbon atoms, 1 to 16 carbon atoms, 1 to 12 carbon atoms, 1 to 8 carbon atoms, or 1 to 4 carbon atoms, unless otherwise specified. The alkylene group may be a linear, branched or cyclic alkylene group and may optionally be substituted with one or more substituents.

In the present application, the term monovalent or divalent hydrocarbon group may mean a monovalent or divalent residue derived from a compound consisting of carbon and hydrogen or a derivative thereof, unless otherwise specified. Here, as the compound consisting of carbon and hydrogen, alkane, alkene, alkyne or aromatic hydrocarbon can be exemplified.

The term alkane herein may mean alkane having 1 to 20 carbon atoms, 1 to 16 carbon atoms, 1 to 12 carbon atoms, 1 to 8 carbon atoms or 1 to 4 carbon atoms, unless otherwise specified. The alkane may be linear, branched or cyclic and may optionally be substituted with one or more substituents. As the monovalent residue derived from alkane, alkyl can be exemplified, and as the divalent residue, alkylene can be exemplified.

The term alkene herein may mean alkene having 2 to 20 carbon atoms, 2 to 16 carbon atoms, 2 to 12 carbon atoms, 2 to 8 carbon atoms, or 2 to 4 carbon atoms, unless otherwise specified. The alkene may be linear, branched or cyclic and may optionally be substituted with one or more substituents. As the monovalent residue derived from alkene, alkenyl can be exemplified, and as the divalent residue, alkenylene can be exemplified.

The term alkyne may mean alkyne having 2 to 20 carbon atoms, 2 to 16 carbon atoms, 2 to 12 carbon atoms, 2 to 8 carbon atoms, or 2 to 4 carbon atoms, unless otherwise specified. The alkyne may be linear, branched or cyclic and may optionally be substituted with one or more substituents. As the monovalent residue derived from alkyne, alkynyl can be exemplified, and as the divalent residue, alkynylene can be exemplified.

In addition, the monovalent residue derived from an aromatic hydrocarbon may be referred to as aryl in the present specification, and the divalent residue may be referred to as arylene. The term aryl group or arylene group herein may mean, unless otherwise specified, a monovalent or divalent residue derived from a compound comprising one benzene ring structure or a structure in which two or more benzene rings are linked while sharing one or two carbon atoms, or linked by any linker, or a derivative thereof. The aryl group or the arylene group may be, for example, an aryl group having 6 to 30 carbon atoms, 6 to 25 carbon atoms, 6 to 21 carbon atoms, 6 to 18 carbon atoms or 6 to 13 carbon atoms, unless otherwise specified.

In the present application, as the substituent with which a substituent such as alkane, alkene, alkyne, alkyl, alkylene, alkenyl, alkenylene, alkynyl, alkynylene, aromatic hydrocarbon, an aryl group or an arylene group or other substituents may be optionally substituted, a hydroxy group, a halogen atom such as fluorine or chlorine, a carboxyl group, a glycidyl group, an acryloyl group, a methacryloyl group, an acryloyloxy group, a methacryloyloxy group, a thiol group, an alkyl group, an alkenyl group, alkynyl group, an alkylene group, an alkenylene group, an alkynylene group, an alkoxy group or an aryl group, and the like can be exemplified, but is not limited thereto.

In Formula 1, —X—Y may be substituted at the ortho, meta or para position.

As the monomer capable of forming the unit of Formula 1, 4-propylstyrene, 4-butylstyrene, 4-pentylstyrene, 4-hexylstyrene, 4-octylstyrene, 4-decylstyrene, 4-dodecylstyrene, 4-tetradecylstyrene, 4-hexadecylstyrene, 4-octadecylstyrene, 4-eicocyl styrene, 4-propyloxystyrene, 4-butyloxystyrene, 4-pentyloxystyrene, 4-hexyloxystyrene, 4-octyloxystyrene, 4-decyloxystyrene, 4-dodecyloxystyrene, 4-tetradecyloxystyrene, 4-hexadecyloxystyrene, 4-octadecyloxystyrene, 4-eicoyloxystyrene, 1-((propoxy)methyl))-4-vinylbenzene, 1-((butoxy)methyl))-4-vinylbenzene, 1-((pentoxy)methyl))-4-vinylbenzene, 1-((hexyloxy)methyl))-4-vinylbenzene, 1-((octyloxy)methyl))-4-vinylbenzene, 1-((decyloxy)methyl))-4-vinylbenzene, 1-((dodecyloxy)methyl))-4-vinylbenzene, 1-((tetradecyloxy)methyl))-4-vinylbenzene, 1-((hexadecyloxy)methyl))-4-vinylbenzene, 1-((octadecyloxy)methyl))-4-vinylbenzene or 1-((eicosyloxy) methyl)-4-vinylbenzene, and the like can be exemplified, but is not limited thereto.

The random copolymer containing a unit of Formula 1 can effectively form a neutral layer capable of inducing the vertical orientation of various block copolymers, for example, a block copolymer comprising a block of a unit of Formula 1 above or a block of a unit of the structure similar thereto, as described below.

The benzene ring in the unit of Formula 1 may be substituted with at least one cross-linkable functional group, for example, a hydroxy group, an epoxy group, an isocyanate group, a glycidyl group, a substituent of Formula 8 to be described below, a benzoylphenoxy group, an alkenyloxycarbonyl group, a (meth) acryloyl group or an alkenyloxyalkyl group, and the like.

Also, the functional group as above, for example, a hydroxy group, and the like may be bonded to the terminal of the random copolymer containing the unit of Formula 1. The random copolymer having a hydroxy group thus bonded to the terminal may be prepared by polymerizing a random copolymer using an RAFT (reversible addition fragmentation chain transfer) agent or an ATRP (atom transfer radical polymerization) initiator, and the like.

The ratio of the unit of Formula 1 in the random copolymer is not particularly limited, and this ratio can be adjusted, for example, depending on the kind of the block copolymer to which the neutral layer is applied. In one example, the unit of Formula 1 above in the random copolymer may have a ratio in a range of about 10% by mole to 90% by mole. In another example, the ratio may be at least 15% by mole, at least 20% by mole, at least 25% by mole, at least 30% by mole, at least 35% by mole, at least 40% by mole, or at least 45% by mole, and not more than 85% by mole, not more than 80% by mole, not more than 75% by mole, not more than 70% by mole, not more than 65% by mole, not more than 60% by mole, not more than 55% by mole, or not more than 50% by mole or so, but is not limited thereto.

The random copolymer may contain an additional unit together with the unit of Formula 1. As the additional unit, for example, any one of the units represented by any one of Formulas 3 to 7 below can be exemplified.

Hereinafter, the unit represented by any one of Formulas 3 to 7 above may be referred to as a second unit.

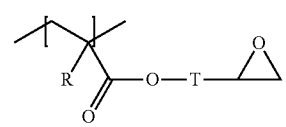

[Formula 3]

In Formula 3, R is hydrogen or an alkyl group, and T is a single bond or a divalent hydrocarbon group with or without a hetero atom.

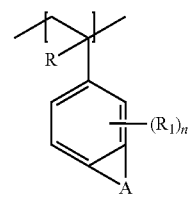

[Formula 4]

In Formula 4, R is hydrogen or an alkyl group, A is an alkylene group, R1 may be hydrogen, a halogen atom, an alkyl group or a haloalkyl group, and n is a number in a range of 1 to 3.

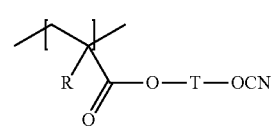

[Formula 5]

In Formula 5, R is hydrogen or an alkyl group, and T is a divalent hydrocarbon group with or without a hetero atom.

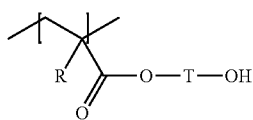

[Formula 6]

In Formula 6, R is hydrogen or an alkyl group having 1 to 4 carbon atoms, and T is a divalent hydrocarbon group with or without a hetero atom.

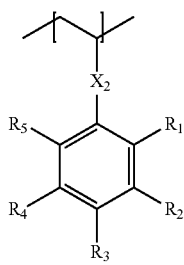

[Formula 7]

In Formula 7, $X_2$ is a single bond, an oxygen atom, a sulfur atom, $-S(=O)_2-$, an alkylene group, an alkenylene group, an alkynylene group, $-C(=O)-X_3-$ or $-X_3-C(=O)-$, where $X_3$ is a single bond, an oxygen atom, a sulfur atom, $-S(=O)_2-$, an alkylene group, an alkenylene group or an alkynylene group, and $R_1$ to $R_5$ are each independently hydrogen, an alkyl group, a haloalkyl group, a halogen atom or a cross-linkable functional group, where the number of the cross-linkable functional groups contained in $R_1$ to $R_5$ is one or more.

In another example, the alkyl group in Formulas 3 to 7 may be an alkyl group having 1 to 20 carbon atoms, 1 to 16 carbon atoms, 1 to 12 carbon atoms, 1 to 8 carbon atoms, or 1 to 4 carbon atoms. Such an alkyl group may be linear, branched or cyclic and may optionally be substituted with one or more of the foregoing substituents.

The haloalkyl group in Formula 4 is an alkyl group in which at least one hydrogen atom is substituted with a halogen atom, where the alkyl group may be an alkyl group having 1 to 20 carbon atoms, 1 to 16 carbon atoms, 1 to 12 carbon atoms, 1 to 8 carbon atoms, or 1 to 4 carbon atoms. Such a haloalkyl group may be linear, branched or cyclic and may optionally be substituted with one or more of the foregoing substituents. Here, as the halogen atom with which the hydrogen atom is substituted, fluorine or chlorine and the like can be also exemplified.

In another example, the alkylene group of A in Formula 4 may be an alkylene group having 1 to 20 carbon atoms, 1 to 16 carbon atoms, 1 to 12 carbon atoms, 1 to 8 carbon atoms, or 1 to 4 carbon atoms. Such an alkylene group may be linear, branched or cyclic and may optionally be substituted with one or more of the foregoing substituents.

The basic definition of the divalent hydrocarbon group in Formulas 3 to 7 is as described above. The divalent hydrocarbon group of Formulas 3 to 7 may further include a hetero atom, if necessary. Here, the hetero atom is a hetero atom for carbon, and for example, includes oxygen, nitrogen or sulfur, and the like. 1 to 4 or less of such hetero atoms may be included in the divalent hydrocarbon group of Formulas 3 to 7.

Here, the type of the cross-linkable functional group included in Formula 7 is not particularly limited. For example, the cross-linkable functional group may be a photo-cross-linkable functional group or a thermo-cross-linkable functional group. As the photo-cross-linkable functional group, a benzoylphenoxy group, an alkenyloxycarbonyl group, a (meth) acryloyl group or an alkenyloxyalkyl group, and the like can be exemplified, but is not limited thereto.

As the cross-linkable functional group which can be included in the unit of Formula 7, for example, a functional group represented by Formula 8 below can also be used.

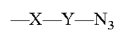 [Formula 8]

In Formula 8, Y is a single bond, an alkylene group, an alkenylene group or an alkynylene group, and X is a single bond, an oxygen atom, a sulfur atom, $-S(=O)_2-$, an alkylene group, an alkenylene group, alkynylene group, $-C(=O))-X_1-$ or $-X_1-C(=O)-$, where $X_1$ is a single bond, an oxygen atom, a sulfur atom, $-S(=O)_2-$, an alkylene group, an alkenylene group or an alkynylene group.

The functional group of Formula 8 is a substituent in which a cross-linkable azide residue is present at the terminal, and such a functional group can be cross-linked.

In another example, Y in Formula 8 may be an alkylene group having 1 to 20 carbon atoms, 1 to 16 carbon atoms, 1 to 12 carbon atoms, 1 to 8 carbon atoms, or 1 to 4 carbon atoms.

Also, in another example, X in Formula 8 may be a single bond, an oxygen atom, $-C(=O)-O-$ or $-O-C(=O)-$, but is not limited thereto.

Examples of the monomers capable of forming the units of Formulas 3 to 7 are not particularly limited. For example, as the monomer capable of forming the unit represented by Formula 3, glycidyl (meth)acrylate and the like can be exemplified, as the monomer capable of forming the unit represented by Formula 4, 4-vinylbenzocyclobutene and the like can be exemplified, as the monomer capable of forming the unit represented by Formula 5, 2-isocyanatoethyl acrylate, 2-isocyanatoethyl (meth)acrylate, 4-isocyanatobutyl acrylate or 4-isocyanatobutyl (meth)acrylate and the like can be exemplified, and as the monomer capable of forming the unit represented by Formula 6, hydroxymethyl acrylate, hydroxymethyl (meth)acrylate, 2-hydroxyethyl acrylate, 2-hydroxyethyl (meth)acrylate, 2-hydroxypropyl acrylate, 2-hydroxypropyl (meth)acrylate, 3-hydroxypropyl acrylate, 3-hydroxypropyl (meth)acrylate, 2-hydroxybutyl acrylate, 2-hydroxybutyl (meth)acrylate, 4-hydroxybutyl acrylate, 4-hydroxybutyl (meth)acrylate, 6-hydroxyhexyl acrylate or 6-hydroxyhexyl (meth)acrylate and the like can be exemplified, without being limited thereto. In addition, as the monomer capable of forming the unit of Formula 7, a monomer and the like, in which a monomer such as styrene is substituted with one or more of the foregoing cross-linkable functional groups, for example, a monomer of Formula 8 above or a benzoylphenoxy group, an alkenyloxycarbonyl group, a (meth)acryloyl group or an alkenyloxyalkyl group and the like, can be exemplified.

The ratio of the second unit in the random copolymer is not particularly limited, and this ratio can be adjusted, for example, depending on the kind of the block copolymer to which the neutral layer is applied. In one example, the ratio of the second units in the random copolymer may be about 1% by mole to 20% by mole or so, but is not limited thereto. In another example, the ratio may be 18% by mole or less, 16% by mole or less, 14% by mole or less, 12% by mole or less, 10% by mole or less, 8% by mole or less, 6% by mole or less, or 4% by mole or less, or so.

The random copolymer may include an additional unit (hereinafter, third unit) together with the unit of Formula 1 and the second unit above. As such a third unit, a polymerized unit derived from a (meth)acrylic acid ester compound such as methyl (meth)acrylate, ethyl (meth)acrylate, n-propyl (meth)acrylate, isopropyl (meth)acrylate, n-butyl (eth) acrylate, isobutyl (meth)acrylate, t-butyl (meth)acrylate, n-hexyl (meth)acrylate or octyl (meth)acrylate, a polymerized unit derived from vinyl pyridine such as 2-vinyl pyridine or 4-vinyl pyridine, or a polymerized unit derived from a styrenic monomer such as styrene, 4-trimethylsilylstyrene, 2,3,4,5,6-pentafluorostyrene, 3,4,5-trifluorostyrene, 2,4,6-trifluorostyrene or 4-fluorostyrene can be exemplified, but is not limited thereto.

In one example, the random copolymer may further include, as the third unit, a unit represented by Formula 9 below.

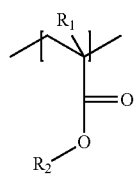

[Formula 9]

In Formula 9, $R_1$ is hydrogen or an alkyl group, and $R_2$ is an alkyl group.

In another example, $R_1$ in Formula 9 may be hydrogen or an alkyl group having 1 to 4 carbon atoms; hydrogen or a methyl group; or a methyl group.

Also, in another example, $R_2$ in Formula 9 may be an alkyl group having 1 to 20 carbon atoms, 1 to 16 carbon atoms, 1 to 12 carbon atoms, 1 to 8 carbon atoms, or 1 to 4 carbon atoms.

Here, the polymerized unit derived from a certain monomer may mean a skeleton structure in which each monomer as described above is polymerized and formed in the random copolymer.

When the third unit is included in the random copolymer, the ratio is not particularly limited and can be adjusted, for example, depending on the kind of the block copolymer to which the neutral layer is applied. In one example, the ratio of the third unit in the random copolymer may be about 10% by mole to 90% by mole or so, but is not limited thereto. In another example, the ratio may be at least about 15% by mole, at least 20% by mole, at least 25% by mole, at least 30% by mole, at least 35% by mole, at least 40% by mole, or at least 45% by mole, and also 80% by mole or less, 75% by mole or less, 70% by mole or less, 65% by mole or less, 60% by mole or less, or 55% by mole or less.

The random copolymer may have a number average molecular weight (Mn) in a range of, for example, 2,000 to 500,000. In another example, the number average molecular weight may be 3,000 or more, 4,000 or more, 5,000 or more, 6,000 or more, 7,000 or more, 8,000 or more, 9,000 or more, 10,000 or more, 20,000 or more, 30,000 or more, 40,000 or more, 50,000 or more, 60,000 or more, 70,000 or more, 80,000 or more, 90,000 or more, or about 100,000 or more or so. In another example, the number average molecular weight may be about 400,000 or less, about 300,000 or less, or about 200,000 or less or so. In this specification, the term number average molecular weight is a value converted to standard polystyrene measured by using GPC (Gel Permeation Chromatograph), and the term molecular weight means a number average molecular weight, unless otherwise specified. The molecular weight of the random copolymer can be adjusted in consideration of the physical properties and the like of the neutral layer comprising the random copolymer.

The method for producing the random copolymer is not particularly limited. For example, the random copolymer may be prepared by applying a free radical polymerization method or an LRP (Living Radical Polymerization) method and the like. As an example of the LRP method, anion polymerization in which polymerization is carried out in the presence of an inorganic acid salt such as an alkali metal or alkaline earth metal salt or an organoaluminum compound using an organic rare earth metal complex or an organic alkali metal compound as an initiator, an atom transfer radical polymerization method (ATRP) using an atom transfer radical polymerization agent as a polymerization inhibitor, an ARGET (Activators Regenerated by Electron Transfer) atom transfer radical polymerization method (ATRP), which uses an atom transfer radical polymerization agent as a polymerization initiator, but performs polymerization under an organic or inorganic reducing agent that generates electrons, an ICAR (Initiators for Continuous Activator Regeneration) atom transfer radical polymerization method, a polymerization method by reversible addition-fragmentation chain transfer (RAFT) using an inorganic reducing agent and a reversible addition-fragmentation chain transfer agent or a method of using an organotellurium compound as an initiator, and the like can be exemplified, and a suitable method may be employed among the above methods.

The kind of the radical initiator that can be used in the polymerization process is not particularly limited. For example, an azo initiator such as AIBN (azobisisobutyronitrile) or 2,2'-azobis-(2,4-dimethylvaleronitrile) or a peroxide initiator such as BPO (benzoyl peroxide) or DTBP (di-tert-butyl peroxide) may be applied, and for example, like a method using thermal self initiation of a styrenic monomer, a polymerization method using no initiator may be also applied depending on the type of the monomer.

The polymerization process can be carried out, for example, in a suitable solvent, and in this case, as an applicable solvent, a solvent such as methylene chloride, 1,2-dichloroethane, chlorobenzene, dichlorobenzene, benzene, toluene, anisole, acetone, chloroform, tetrahydrofuran, dioxane, monoglyme, diglyme, dimethylformamide, dimethylsulfoxide or dimethylacetamide can be exemplified, but is not limited thereto. After forming the random copolymer, the random copolymer can be obtained by precipitation using a non-solvent, where as the usable non-solvent, an alcohol such as methanol, ethanol, n-propanol or isopropanol, a glycol such as ethylene glycol, an ether solvent such as n-hexane, cyclohexane, n-heptane or petroleum ether, and the like can be exemplified, but is not limited thereto.

In the field of polymer synthesis, a method for producing a polymer by performing polymerization depending on a monomer forming the polymer is known, and any of the above methods may be applied upon producing the random copolymer of the present application.

The neutral layer composition comprising the random copolymer as described above may comprise only the predetermined random copolymer or, if necessary, other components in addition to the random copolymer. The neutral layer composition may comprise at least the random copolymer as the main component. The inclusion as the main component herein may mean that the corresponding composition comprises only the random copolymer, or comprises 50% by weight or more, 55% by weight or more, 60% by weight or more, 65% by weight or more, 70% by weight or more, 75% by weight or more, 80% by weight or more, 85% by weight or more, or 90% by weight or more. In another example, the ratio may be about 100% by weight or less or about 99% by weight or less or so. In addition, as other components that can be included together with the random copolymer, for example, thermal initiators or photoinitiators necessary when the random copolymer contains the above-mentioned photo-cross-linkable or thermo-cross-linkable functional group and the like can be exemplified.

The present application also relates to a neutral layer comprising the random copolymer. In the present application, the term neutral layer means a layer capable of inducing the vertical orientation of the block copolymer as described above.

The neutral layer may be formed on a suitable substrate. As the substrate on which the neutral layer is formed, a silicon wafer, a silicon oxide substrate, a silicon nitride substrate, or a cross-linked PET (poly(ethylene terephthalate)) film, and the like can be exemplified, but is not limited thereto.

The neutral layer can be formed using the neutral layer composition as described above. For example, the process of forming the neutral layer may comprise steps of coating the neutral layer composition on the substrate and fixing the layer of the coated neutral layer composition. Here, the method for coating the neutral layer composition on the substrate is not particularly limited, and for example, a method such as bar coating, spin coating or comma coating may be applied, and coating by a roll-to-roll method may be also applied.

Furthermore, the method for fixing the layer of the neutral layer composition is not particularly limited, and for example, a method for inducing covalent bonds between the layer and the substrate by a suitable manner or inducing a chemical cross-linking reaction in the layer, and the like may be applied. For example, when the above process is performed by heat treatment, the heat treatment may be controlled within a range of about 100° C. to 250° C. or about 100° C. to 200° C. Also, the time required for the heat treatment may be varied as needed, and may be adjusted, for example, within a range of about 1 minute to 72 hours or about 1 minute to 24 hours. The temperature and time of the heat treatment may be adjusted to an appropriate level in consideration of the type of the functional group of the random copolymer in the neutral layer composition, and the like.

The neutral layer may have, for example, a thickness of about 2 nm to 100 nm, and in another example, it may have a thickness of about 2 nm to 50 nm. Within the thickness range, there may be benefits that the surface uniformity of the neutral layer can be maintained, the vertical orientation of the block copolymer can be induced, and then etching selectivity cannot be damaged during the etching process.

The present application also relates to a laminate comprising a neutral layer comprising the random copolymer, and a polymer film formed on one surface of the neutral layer and comprising a block copolymer having a first block and a second block chemically distinct from the first block.

The polymer film in the above laminate may be used in various applications, and for example, may be used in various electron or electronic elements, a process of forming the pattern or a recording medium such as a magnetic storage medium and a flash memory or a biosensor and the like, or a process of manufacturing a separation membrane, and the like.

In one example, the block copolymer in the polymer film may embody a cyclic structure, including a sphere, a cylinder, a gyroid or a lamellar, and the like through self-assembly. In the case of the sphere or the lamella of the above structures, the block copolymer may be in a vertically oriented state.

For example, in the segments of the first or second block or other blocks covalently bonded thereto in the block copolymer, other segments may be vertically oriented, while forming a regular structure such as a lamellar shape or a cylinder shape.

The block copolymer that can be included in the polymer film in the above-described laminate is not particularly limited.

For example, the block copolymer may include, as the first block, a repeating unit represented by Formula 1 as described above.

Also, in the block copolymer, the kind of the second block included together with the first block is not particularly limited. For example, as the second block, a polyvinyl pyrrolidone block, a polylactic acid block, a polyvinyl pyridine block, a polystyrene block such as polystyrene or polytrimethylsilyl styrene, a poly(perfluorostyrene) block such as poly(2,3,4,5,6-pentafluorostyrene), a poly(meth) acrylate block such as poly(methylmethacrylate), a polyalkylene oxide block such as polyethylene oxide, a polybutadiene block, a polyisoprene block, or a polyolefin block such as polyethylene can be exemplified.

As the second block, a block including the units of Formulas 3 to 7 and/or the unit of Formula 9, as described above, and the like may be also used.

The block copolymer of the present application may be a diblock copolymer including the first block and the second block as described above, or a multi-block copolymer including two or more of at least one of the first block and the second block, or another kind of a third block.

The number average molecular weight (Mn) of the block copolymer may be, for example, in the range of 2,000 to 500,000. The block copolymer may have a polydispersity (Mw/Mn) in a range of 1.01 to 1.50.

In this range, the block copolymer can exhibit proper self-assembly characteristics. The number average molecular weight of the block copolymer and the like can be adjusted in consideration of the desired self-assembly structure and the like.

When the block copolymer comprises at least the first and second blocks, the first block, for example, the block including the unit of Formula 1 as described above, in the block copolymer may have a ratio in the range of 10% by mole to 90% by mole.

The specific method for producing the block copolymer in the present application is not particularly limited as long as it comprises the step of forming at least one block of the block copolymer using the above-mentioned monomer.

For example, the block copolymer can be prepared by the LRP (Living Radical Polymerization) method using the above monomers. For example, there are anion polymerization in which polymerization is carried out in the presence of an inorganic acid salt such as an alkali metal or alkaline earth metal salt or an organoaluminum compound using an organic rare earth metal complex or an organic alkali metal compound as an initiator, an atom transfer radical polymerization method (ATRP) using an atom transfer radical polymerization agent as a polymerization inhibitor, an ARGET (Activators Regenerated by Electron Transfer) atom transfer radical polymerization method (ATRP), which uses an atom transfer radical polymerization agent as a polymerization initiator, but performs polymerization under an organic or inorganic reducing agent that generates electrons, an ICAR (Initiators for Continuous Activator Regeneration) atom transfer radical polymerization method, a polymerization method by reversible addition-fragmentation chain transfer (RAFT) using an inorganic reducing agent and a reversible addition-fragmentation chain transfer agent or a method of using an organotellurium compound as an initiator, and the like, and a suitable method may be selected and applied among the above methods.

For example, the block copolymer can be prepared in a manner which comprises polymerizing a reactant containing monomers capable of forming the block in the presence of a radical initiator and a living radical polymerization reagent by the living radical polymerization method.

The method for forming other blocks included in the copolymer, together with the block formed by using the monomer, upon producing the block copolymer is not particularly limited, and the other blocks may be formed by selecting a suitable monomer in consideration of the kind of the desired block.

The process for preparing the block copolymer may further comprise, for example, a step of precipitating the polymerization product produced through the above process in the non-solvent.

The kind of the radical initiator is not particularly limited, may be appropriately selected in consideration of the polymerization efficiency, and for example, an azo compound such as AIBN (azobisisobutyronitrile) or 2,2'-azobis-(2,4-dimethylvaleronitrile), or peroxide series such as BOP (benzoyl peroxide) or DTBP (di-t-butyl peroxide) may be used.

The living radical polymerization process can be carried out in a solvent such as, for example, methylene chloride, 1,2-dichloroethane, chlorobenzene, dichlorobenzene, benzene, toluene, acetone, chloroform, tetrahydrofuran, dioxane, monoglyme, diglyme, dimethylformamide, dimethylsulfoxide or dimethylacetamide.

As the non-solvent, an alcohol such as methanol, ethanol, normal propanol or isopropanol, a glycol such as ethylene glycol, ether series such as n-hexane, cyclohexane, n-heptane or petroleum ether, and the like can be used, but is not limited thereto.

The method for forming the polymer film as above using the block copolymer is not particularly limited. For example, the method may comprise forming the polymer film comprising the block copolymer, in a self-assembled state, on the neutral layer. For example, the method may comprise a process of forming a layer of the block copolymer or a coating liquid in which the block copolymer is diluted in an appropriate solvent, on the neutral layer by application or the like and, if necessary, annealing or heat-treating the layer.

The annealing or heat treatment may be performed, for example, based on the phase transition temperature or the glass transition temperature of the block copolymer, and for example, may be performed at a temperature above the glass transition temperature or the phase transition temperature. The time for performing this heat treatment is not particularly limited, and the heat treatment can be performed within a range of, for example, about 1 minute to 72 hours, but this can be changed as needed. In addition, the heat treatment temperature of the polymer thin film may be, for example, 100° C. to 250° C. or so, but this can be changed in consideration of the block copolymer to be used.

In another example, the formed layer may be also subjected to solvent annealing in a non-polar solvent and/or a polar solvent at room temperature for about 1 minute to 72 hours.

The present application also relates to a method for forming a pattern. The method may comprise, for example, selectively removing the first or second block of the block copolymer from the polymer film of the laminate. The method may be a method for forming a pattern on the substrate. For example, the method may comprise forming the polymer film comprising the block copolymer on the substrate, selectively removing one or more blocks of the block copolymer present in the film, and then etching the substrate. In this way, it is possible to form, for example, nanoscale fine patterns. In addition, various types of patterns such as nanorods or nanoholes can be formed through the above method depending on the type of the block copolymer in the polymer film. If necessary, the block copolymer may be mixed with other copolymers or homopolymers for pattern formation. The type of the substrate to be applied to this method is not particularly limited, which may be selected as needed, and for example, silicon oxide or the like may be applied.

For example, the method can form a nanoscale pattern of silicon oxide that exhibits a high aspect ratio. For example, after forming the polymer film on silicon oxide and selectively removing any one block of the block copolymer in a state where the block copolymer in the polymer film forms a predetermined structure, silicon oxide may be etched in various ways, for example, reactive ion etching or the like to embody various shapes including patterns of nanorods or nanoholes. In addition, it is possible to embody nano patterns having a large aspect ratio through this method.

For example, the pattern can be implemented on a scale of several tens of nanometers, and such a pattern can be utilized in various applications including, for example, next-generation information electronic magnetic recording media and the like.

Here, the method for selectively removing any one block of the block copolymer is not particularly limited, and for example, a method for removing a relatively soft block by irradiating the polymer film with an appropriate electromagnetic wave, for example, ultraviolet and the like can be used. In this case, the ultraviolet irradiation conditions are determined depending on the type of block of the block copolymer, and for example, the method can be performed, for example, by irradiating it with ultraviolet having a wavelength of about 254 nm for 1 minute to 60 minutes.

In addition, the ultraviolet irradiation may be followed by a step of treating the polymer film with an acid or the like to further remove the segment decomposed by ultraviolet.

In addition, the step of etching the substrate using a mask the polymer film, in which the block is selectively removed, is not particularly limited, which may be performed, for example, through the reactive ion etching step using $CF_4/Ar$ ions or the like, and following this process, a step of removing the polymer film from the substrate by an oxygen plasma treatment or the like can be also performed.

Advantageous Effects

The present application may provide a neutral layer composition capable of forming a neutral layer that can be effectively applied to formation of a polymer film comprising a vertically oriented self-assembly block copolymer.

BRIEF DESCRIPTION OF DRAWINGS

FIGS. 1 and 2 are views showing orientation results of block copolymers in Comparative Examples and Examples.

MODE FOR INVENTION

Hereinafter, the present application will be described in detail by way of examples according to the present application and comparative examples, but the scope of the present application is not limited by the following examples.

1. NMR Measurement

The NMR analysis was performed at room temperature using an NMR spectrometer including a Varian Unity Inova (500 MHz) spectrometer with a triple resonance 5 mm probe. An analyte was diluted in a solvent for measuring NMR (CDCl$_3$) to a concentration of about 10 mg/ml and used, and chemical shifts were expressed in ppm.

<Application Abbreviations> br=wide signal, s=singlet, d=doublet, dd=double doublet, t=triplet, dt=double triplet, q=quartet, p=quintet, m=muliplet.

2. GPC (Gel Permeation Chromatograph)

The number average molecular weight (Mn) and the molecular weight distribution were measured using GPC (Gel Permeation Chromatography). Analytes such as the block copolymers of Examples or Comparative Examples or macroinitiators are introduced into a 5 mL vial and diluted in THF (tetrahydrofuran) so as to be a concentration of about 1 mg/mL. Then, the calibration standard sample and the sample to be analyzed were filtered through a syringe filter (pore size: 0.45 µm) and then measured. As an analytical program, ChemStation from Agilent Technologies was used, and the elution time of the sample was compared with the calibration curve to obtain the weight average molecular weight (Mw) and the number average molecular weight (Mn), respectively, and to calculate the molecular weight distribution (PDI) from the ratio (Mw/Mn). The measurement conditions of GPC are as follows.

<GPC Measurement Conditions>

Device: 1200 series from Agilent Technologies
Column: using two PLgel mixed B from Polymer laboratories
Solvent: THF
Column temperature: 35° C.
Sample concentration: 1 mg/mL, 200 L injection
Standard samples: polystyrene (Mp: 3900000, 723000, 316500, 52200, 31400, 7200, 3940, 485)

Preparation Example 1. Synthesis of Compound (A)

A compound (hereinafter, compound (A)), in which in Formula A below, X is a residue of Formula B below, and in Formula B above, T is methylene, m is 1 and Y of Formula A is a dodecyl group, was synthesized by the following method. T of Formula B was linked to the benzene ring, and the oxygen atom was linked to Y, i.e., the dodecyl group. In a 500 mL flask, 4-(chloromethyl)styrene (22.1 g, 144.8 mmol) and 1-dodecanol (30.0 g, 160.1 mmol) were dissolved in 300 mL of tetrahydrofuran (THF) and then the temperature was lowered to 0° C. Sodium hydride (NaH) (7.7 g, 320.8 mmol) was divided in small portions, added thereto, and the mixture was stirred for 1 hour and then heated to 70° C. to be reacted for 24 hours. Upon completing the reaction, the reaction mixture was cooled to room temperature, and then a small amount of water was added thereto on ice water and reacted with sodium hydride remaining after the reaction, followed by removing the solid content through a filter. After removing tetrahydrofuran which is a reaction solvent, the reaction mixture was subjected to fractional extraction with dichloromethane (DCM)/secondary pure water to collect an organic layer, and then the resulting compound was subjected to column chromatography using hexane/dichloromethane as a mobile phase to obtain a transparent liquid compound (A) (23.9 g, 79.0 mmol).

<NMR Analysis Result>

$^1$H-NMR (CDCl$_3$): δ 7.39 (dd, 2H); δ 7.30 (dd, 2H); δ 6.71 (dd, 1H); δ 5.74 (d, 1H); 5.23 (d, 1H); δ 4.49 (s, 2H); δ 3.46 (t, 2H); δ 1.61 (p, 2H); δ 1.37-1.26 (m, 16H); δ 0.89 (t, 3H).

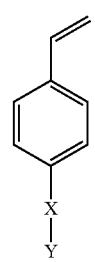

[Formula A]

[Formula B]

Preparation Example 2. Synthesis of Block Copolymer (A)

AIBN (azobisisobutyronitrile) and an RAFT reagent (CPDB, 2-cyanoprop-2-yl-benzodithioate) as thermal initiators were reacted with methyl methacrylate (MMA) to synthesize a macroinitiator (number average molecular weight (Mn): 8500, molecular weight distribution (Mw/Mn): 1.16). The synthesized macroinitiator and the compound (A) and AIBN (azobisisobutyronitrile) were diluted in anisole at an equivalent ratio of 1:100:0.5 (macroinitiator:compound (A):AIBN) to prepare a solution having a solid content concentration of about 30% by weight. Thereafter, the mixed liquid was reacted in a nitrogen atmosphere at 70° C. for 4 hours to obtain a block copolymer (A). The number average molecular weight (Mn) and the molecular weight distribution (Mw/Mn) of the block copolymer (A) were 14800 and 1.16, respectively. The block copolymer comprises the repeating unit derived from the methyl methacrylate and the repeating unit derived from the compound A, that is, the unit in which in a state where —X—Y in Formula 1 of claim 1 is linked to the para position, X is a unit of Formula 2 of claim 1, where T is methylene and m is 1, and Y is a dodecyl group (T in Formula 2 is linked to the benzene ring, and the oxygen atom is linked to Y, i.e., the dodecyl group).

Preparation Example 3. Synthesis of Random Copolymer (B)

A random copolymer (B) for a neutral layer was synthesized by using methyl methacrylate (MMA), the compound (A) and glycidyl methacrylate (GMA). MMA, the compound (A), GMA and AIBN were diluted in anisole at an equivalent ratio of 50:48:2:0.5 (MMA:compound (A):GMA:AIBN) to prepare a solution having a solid content concentration of about 60% by weight. Thereafter, the mixed liquid was reacted in a nitrogen atmosphere at 60° C. for 10 hours to obtain a random copolymer (B). The number average molecular weight (Mn) and the molecular weight distribution (Mw/Mn) of the random copolymer (B) were 106600 and 2.50, respectively.

Comparative Example 1

Self-Assembly of the Block Copolymer (A)

A self-assembled polymer film was formed using the block copolymer (A) of Preparation Example 2 and the results were confirmed. Specifically, the copolymer was dissolved in toluene at a concentration of about 1.0% by weight, and the prepared coating liquid was spin-coated on a silicon wafer at a speed of 3000 rpm for 60 seconds and then subjected to thermal annealing at about 160° C. to form a film comprising the self-assembled block copolymer. FIG. 1 is an SEM image of the polymer film formed as described above. It can be confirmed from the drawing that the orientation of the polymer film has been not properly formed.

Example 1

Self-Assembly of the Block Copolymer (A) Introducing the Neutral Layer of the Random Copolymer (B)

Using the random copolymer (B) of Preparation Example 3 and the block copolymer (A) of Preparation Example 2, a cross-linked neutral layer and a self-assembled polymer film were formed, respectively, and the results were confirmed. Specifically, the random copolymer (B) of Preparation Example 3 was first dissolved in toluene at a concentration of about 1.0% by weight, and the prepared coating liquid was spin-coated on a silicon wafer at a speed of 3000 rpm for 60 seconds, and then subjected to thermal cross-linking at about 160° C. to form a cross-linked neutral layer. The block copolymer (A) was dissolved in toluene at a concentration of about 1.0% by weight, and the prepared coating solution was spin-coated on the neutral layer at a rate of 3000 rpm for 60 seconds, and then subjected to thermal annealing at about 160° C. to form a film comprising the self-assembled block copolymer. FIG. 2 is an SEM image of the polymer film formed as described above. It can be confirmed from the drawing that a proper lamellar vertical orientation structure has been formed.

The invention claimed is:

1. A laminate comprising a neutral layer; and a polymer film formed on one surface of the neutral layer and comprising a block copolymer having a first block and a second block chemically distinct from the first block,
   wherein the neutral layer comprises a random copolymer, and
   wherein the first block of the block copolymer and the random copolymer each contain a unit of Formula 1 below:

[Formula 1]

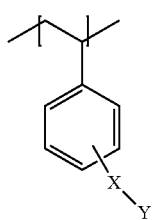

wherein, X is an oxygen atom, —C(=O)—, —OC(=O)—, —C(=O)—O— or a divalent linker represented by Formula 2 below, and Y is a monovalent hydrocarbon group having 3 to 30 carbon atoms;

[Formula 2]

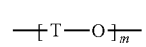

wherein, T is a divalent hydrocarbon group, and m is a number within a range of 1 to 5.

2. The laminate according to claim 1, wherein the unit of Formula 1 in the random copolymer has a ratio in a range of 10% by mole to 90% by mole.

3. The laminate according to claim 1, wherein the random copolymer further comprises a unit represented by any one of Formulas 3 to 7:

[Formula 3]

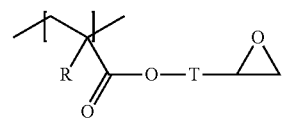

wherein, R is hydrogen or an alkyl group, and T is a single bond or a divalent hydrocarbon group with or without a hetero atom;

[Formula 4]

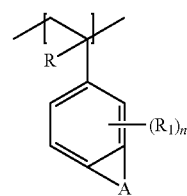

wherein, R is hydrogen or an alkyl group, A is an alkylene group, $R_1$ is hydrogen, a halogen atom, an alkyl group or a haloalkyl group, and n is a number in a range of 1 to 3;

[Formula 5]

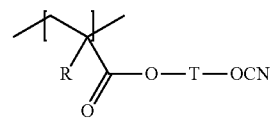

wherein, R is hydrogen or an alkyl group, and T is a divalent hydrocarbon group with or without a hetero atom;

[Formula 6]

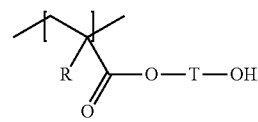

wherein, R is hydrogen or an alkyl group having 1 to 4 carbon atoms, and T is a divalent hydrocarbon group with or without a hetero atom; and

[Formula 7]

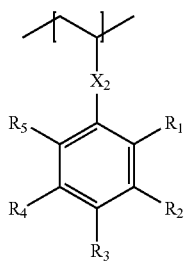

wherein, $X_2$ is a single bond, an oxygen atom, a sulfur atom, $-S(=O)_2-$, an alkylene group, an alkenylene group, an alkynylene group, $-C(=O)-X_3-$ or $-X_3-C(=O)-$, where $X_3$ is a single bond, an oxygen atom, a sulfur atom, $-S(=O)_2-$, an alkylene group, an alkenylene group or an alkynylene group, and $R_1$ to $R_5$ are each independently hydrogen, an alkyl group, a haloalkyl group, a halogen atom or a cross-linkable functional group, where the number of the cross-linkable functional groups contained in $R_1$ to $R_5$ is one or more.

4. The laminate according to claim 1, wherein the unit of Formula 1 is substituted with a cross-linkable functional group.

5. The laminate according to claim 1, wherein the random copolymer further comprises a polymerized unit derived from a (meth)acrylic acid ester compound, a polymerized unit derived from vinylpyridine, or a polymerized unit derived from a styrenic monomer.

6. The laminate according to claim 1, wherein the random copolymer further comprises a unit of Formula 9 below:

[Formula 9]

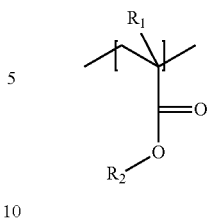

wherein, $R_1$ is hydrogen or an alkyl group, and $R_2$ is an alkyl group.

7. The laminate according to claim 1, wherein the random copolymer has a number average molecular weight in a range of 2000 to 500000.

8. The laminate according to claim 1, wherein the block copolymer embodies a sphere, cylinder, gyroid or lamellar structure.

9. A method for manufacturing the laminate according to claim 1 comprising a step of forming a neutral layer; and a polymer film formed on one surface of the neutral layer and comprising a block copolymer having a first block and a second block chemically distinct from said first block in a self-assembled state, wherein the neutral layer comprises a random copolymer, and wherein the first block of the block copolymer and the random copolymer each contain a unit of Formula 1 defined in claim 1.

10. A method for forming a pattern comprising a step of selectively removing the first or second block of the block copolymer in the polymer film of the laminate of claim 9.

* * * * *